United States Patent
Shribak et al.

(10) Patent No.: US 7,079,247 B2
(45) Date of Patent: Jul. 18, 2006

(54) INSTANTANEOUS POLARIZATION MEASUREMENT SYSTEM AND METHOD

(75) Inventors: Mykhailo Shribak, Woods Hole, MA (US); Rudolf Oldenbourg, Falmouth, MA (US); Paul J. Cronin, Charlestown, MA (US); Clifford C. Hoyt, Somerville, MA (US); Peter J. Miller, Newburyport, MA (US)

(73) Assignee: Marine Biological Laboratory, Woods Hole, MA (US)

( * ) Notice: Subject to any disclaimer, the term of this patent is extended or adjusted under 35 U.S.C. 154(b) by 351 days.

(21) Appl. No.: 10/616,328

(22) Filed: Jul. 8, 2003

(65) Prior Publication Data

US 2005/0007591 A1    Jan. 13, 2005

(51) Int. Cl.
*G01J 4/00* (2006.01)
(52) U.S. Cl. ...................................................... 356/364
(58) Field of Classification Search ................. 356/364
See application file for complete search history.

(56) References Cited

U.S. PATENT DOCUMENTS

| | | | |
|---|---|---|---|
| 5,596,406 A * | 1/1997 | Rosencwaig et al. | 356/327 |
| 5,788,632 A | 8/1998 | Pezzaniti et al. | |
| 5,865,520 A * | 2/1999 | Kavanagh et al. | 353/31 |
| 6,501,548 B1 | 12/2002 | Oldenbourg | |
| 6,563,582 B1 | 5/2003 | Chun | |
| 2002/0091323 A1 * | 7/2002 | Dreher | 600/476 |

* cited by examiner

*Primary Examiner*—Tu T. Nguyen
(74) *Attorney, Agent, or Firm*—Cohen, Pontani, Lieberman & Pavane

(57) ABSTRACT

The invention provides a highly sensitive measurement of retardance and slow axis orientation, accurately and instantaneously, across a full two-dimensional image. There are no moving parts and there need not be any electro-optic tuning as part of the measurement. It is ideally adapted to real-time imaging and is well-suited to use with biological and medical samples, including visualizing structures in oocytes. The invention splits a light beam into several beams, which are analyzed using elliptical polarizers and the resultant intensity is measured. It can be constructed using a single pixilated detector, or several detectors, to achieve high spatial resolution when this is desired.

52 Claims, 15 Drawing Sheets

INSTANTANEOUS POLARIZATION MEASUREMENT SYSTEM AND METHOD

BACKGROUND OF THE INVENTION

1. Field of the Invention

The present invention is directed to measurement of the polarization of light and the polarization properties of samples.

2. Description of the Related Art

The polarization state of light can be measured by taking N measurements of intensity in time-series, while one or more polarizers or waveplates are stepped through a sequence of settings. From the intensities obtained at each of the N settings, the polarization state of incident light is determined. Various arrangements of polarizers and waveplates have been devised for use in determining the Stokes vectors for light of arbitrary polarization.

One may use such an instrument to determine the birefringence or retardance of a sample by illuminating the sample with light of a known polarization state, and measuring the polarization state of light exiting the sample; from the difference between the incident and exit states of polarization, the optical properties of the sample are inferred.

Systems have been devised for imaging measurements of samples with low retardance, such as optical glasses, biological tissue, and cells including oocytes, using imaging detectors such as CCD cameras. Oldenbourg and Mei describe such a system in U.S. Pat. No. 5,521,705 that uses four images to determine retardance magnitude and slow axis orientation angle for a sample that is illuminated with circularly polarized light.

Systems that require taking several exposures in series cannot operate in real-time, and since most utilize video-rate detectors, the total elapsed time can be significant. Further, if there is sample movement during the measurement sequence, inaccurate or unreliable results can be obtained.

So-called instantaneous polarimeter systems have been devised for stress-measurement of samples that exhibit retardances of λ/4 or more. Such systems divide a beam of light from the sample into N sub-beams and perform the required N measurements in parallel, to provide a real-time measurement of polarization state. In some of these, an image is obtained, such as the instrument described in U.S. Pat. No. 6,055,053. This system utilizes partial reflection at beamsplitter elements to divide the beams, which are then delivered to multiple CCD detectors. Another instantaneous polarimeter is described in U.S. Pat. No. 6,441,972, which produces the multiple images at a single CCD detector for easier construction.

The optical system of U.S. Pat. No. 6,441,972 utilizes a plurality of sectored lens slices or a plurality of prisms to produce multiple images at an imaging detector. The prisms are thinner in the center of the beam, to deflect multiple copies of the image outward, into separate images. Alternatively, the lens slices are shifted radially outward for the same purpose (with an attendent loss of light due to the missing space between lens slices). Beyond the performance issues involved, such a system is less than optimal due to its complexity: it requires the fabrication of, and then precise registration of, many lens slices or prisms.

The fruit-grading apparatus of Blit et al.(U.S. Pat. No. 5,526,119) uses a multifaceted prism to create multiple images of a sample. In this system, each prism face is treated with an optical coating so that several images are produced simultaneously at a common CCD detector, each corresponding to a different spectral band. No measurement of polarization is provided by this apparatus.

Retardance imaging has been used to a limited degree in cellular biology research, and in in-vitro fertilization of oocytes, using sequential measurement systems with N=4. But the low measurement speed of such systems has been a barrier to its wider acceptance in these fields.

Overall, no instrument provides the ability to image low-retardance samples in real-time, or nearly so. Such samples may present only a few nanometers of retardance, and for useful imaging, a noise level of 0.2 nm or less in the computed retardance image is beneficial.

It is a goal of the present invention to provide an instrument for measurement of polarization state or sample retardance, which provides greatly improved measurement speed without compromising the accuracy and sensitivity of the readings obtained for low-retardance samples. It is a further goal to provide an apparatus that yields full two-dimensional images of low-retardance biological, medical, and industrial samples in near real-time. Another aim of this invention is to provide these benefits without need for complicated or expensive optical elements. A further goal is to provide designs that greatly reduce polarization errors in the instrument, so the retardance or polarization signals are of high quality. Yet another goal is to provide methods for calibrating and removing any residual errors by data reduction algorithms, so that a high sensitivity and a low noise floor are obtained, comparable to what is achieved by time-sequential measurements.

SUMMARY OF THE INVENTION

The core of the invention involves using one of several optical arrangements to divide light into N distinct beams, which are then analyzed separately using elliptical polarizers optimized for measurements of low retardance samples, and the intensity of these N beams is measured at N detector regions simultaneously. Low-retardance samples to be measured are illuminated with substantially circularly polarized light. Exemplary polarizers and data analysis methods are described in the U.S. patent application titled "Retardance Measurement System and Method" of Shribak and Oldenbourg, filed concurrently herewith and hereby expressly incorporated in its entirety by reference herein; and in U.S. Pat. No. 5,521,705 of Oldenbourg and Mei. These disclosures provide polarization sensing schemes that utilize between 2 and 5 polarization states, which the present invention implements in parallel rather than in time series as in the above references.

The polarization analyzers are so chosen that, taken together, the detectors provide enough information to determine the polarization state of the incident light with high sensitivity, for measurement of low-retardance samples. These are analyzers for two or more approximately circular states of polarization, and in some embodiments one which is substantially a circular polarizer, as will be described in the preferred embodiments.

These analyzers can employ fixed linear polarizer material together with fixed wave-plates, or together with electrically tunable waveplates such as liquid crystal retarders. In the latter case, the retarder apparatus may comprise one or more liquid crystal cells whose electrodes are pixilated into different spatial regions that match the different facets of the beamsplitter. These regions are driven with selected voltages to produce the required retardance in each region so as to realize a chosen polarization analyzer scheme.

In one embodiment, the invention divides the incident light using a single multifaceted prism, which refracts the rays of light to form N separate images corresponding to each facet; these refracted beams are then imaged onto the N multiple detector regions. In optical series with at least two of the facets are elliptical polarization analyzers that selectively transmit a chosen state of polarization for light.

In another embodiment, the invention uses one or more partially reflective beamsplitters to divide the incident light into multiple beams, namely a transmitted beam and a reflected beam. Further subdivision by other splitter elements can be employed to provide the full complement of beams as needed. These form N images at multiple detectors, or are redirected to form N images at a single CCD detector.

In yet another embodiment, the partially reflective beamsplitters are a "polka-dot" type, constructed using spatially patterned reflective elements to minimize the polarization distortion on the beam being measured. This also provides a more achromatic divider than can be readily obtained with multilayer interference coatings.

In another embodiment, the beam is divided by partial reflection at one or more prism beamsplitters, and the optical design provides for substantially equal path length for all the beams, in the region from the initial beamsplitter to the detector.

Variations in responsivity across the detector, or in the optical system generally, either between different points in a given image or between images, are compensated for by measurement of the system's response to light with known states of polarization or to, background images with no sample, or combinations thereof.

In another embodiment, the beamsplitter is a prism with four facets and the polarization analyzers implement the four elliptical states used in the PolScope described by Oldenbourg and Mei, and sold commercially by CRI, Inc. (Woburn Mass.). The system is used together with a circular polarizer in a system for sample analysis, to yield real-time images of sample retardance.

When one or another of these optical systems is constructed, the result is an apparatus for the essentially instantaneous measurement of polarization state across an image; or when used with suitable illumination and suitable analyzers, of sample retardance at all points in an image.

In another embodiment, the above system is used for imaging of living cells. In still another embodiment, the above system is used to image structures in oocytes such as the meiotic spindle or the zona pellucida.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the figures, where like numerals are used to denote like objects or equivalent means.

DETAILED DESCRIPTION OF THE PRESENTLY PREFERRED EMBODIMENTS

Throughout this description, the term image will be used to denote a two-dimensional retardance image. It is nonetheless possible to practice this invention when a two-dimensional image is not desired or necessary, in which case a one-dimensional image, or some other image, or a simple scalar may be obtained instead.

The core of the invention involves dividing a light beam into N sub-beams which are analyzed simultaneously to determine the polarization state of the incident beam. The term sub-beam is used to refer to one of these beams thus divided, and the term sub-image is used to refer to the image formed by a given sub-beam at a detector.

The invention can be practiced with N sub-beams, where N is from 2 to 5 in preferred embodiments. For simplicity and clarity, the figures illustrate the case N=2 or N=3. Systems that divide a beam into a greater number of sub-beams can be constructed as is known in the art, or purchased commercially from Optical Insights (Santa Fe, N.Mex.). Moreover, while the Figures illustrate the case in which the optical axes of the sub-beams are coplanar, this is not a requirement of the invention, and typically will not be the case for N=3 or more.

Two types of beam division systems are treated in this description: those which operate by division of amplitude by partial reflection (DAPR), and those which operate by division of amplitude by shared aperture (DASA). In the special case where the division is performed at a pupil in the optical system, the latter also can be said to operate by division of numerical aperture. Often, though, practical considerations prevent the dividing element from being located exactly at a pupil, and this latter condition is only approximately met.

While these are the preferred embodiments, it is expressly intended that the present invention may be practiced using any apparatus for dividing an incident beam into multiple sub-beams, whether that apparatus works by DAPR, DASA, or any mechanism whatever, as long as it provides sub-beams that are suitable for polarimetric analysis.

In addition, while the disclosed embodiments are constructed for use in the visible spectral range, this is not a limitation of the invention, which may be constructed for use in the ultraviolet, visible, or infrared range. The construction details and detector choice will depend on the spectral range, as is known to those skilled in the art of optical system design.

Figure 1:
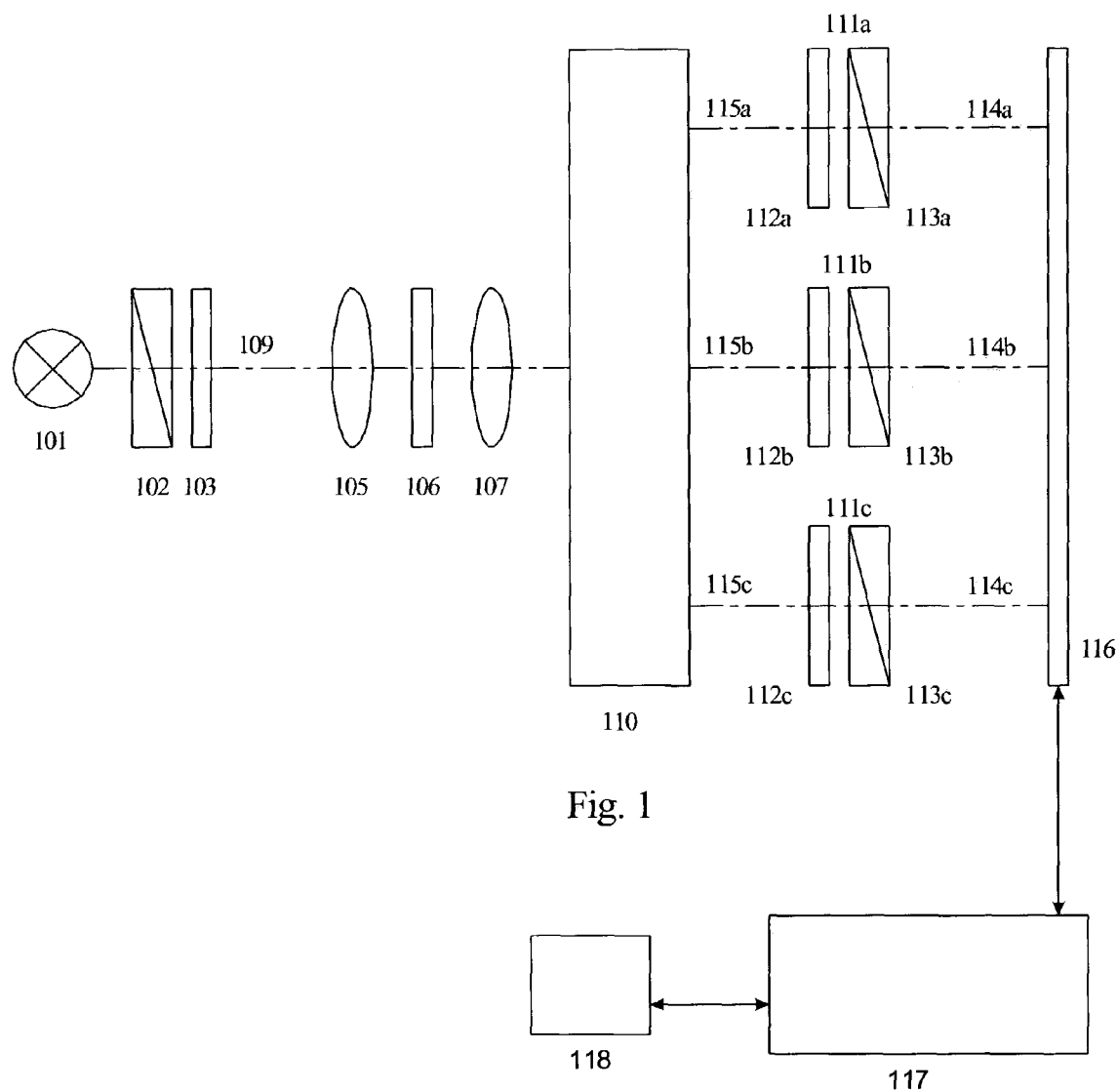
FIG. 1 shows a schematic of the present invention for low retardance samples.

The first preferred embodiment is explained by reference to the Figures. FIG. 1 provides a schematic view of a system with N=3 sub-beams. For such a system, the analyzers 111a–111c implement the three elliptical polarization states described in the concurrently-filed, co-pending Shribak and Oldenbourg U.S. patent application, corresponding to locations on the Poincare sphere that lie on the circle having a latitude of 70° North, at longitudes of 0°, 90°, and 180°. It is used to analyze light that was left-hand polarized, i.e. at the South pole on the Poincare sphere, before passing through the sample.

However, a comparable system can be constructed that operates with analyzers whose polarization states lie on the Poincare sphere on the circle having a latitude of 70° South, at longitudes of 0°, 90°, and 180°. It is also possible to construct a system wherein the set of locations on the Poincare sphere corresponding to the analyzers is x°, x+90°, and x+180°, with the result that the polarization coordinate system is rotated by x/2, and the azimuth angle for the slow axis that is calculated is rotated by this same amount. These generalizations may be applied to all systems discussed below, and are expressly intended as design alternatives when practicing the invention.

Also, while the present invention provides for calculation of the slow-axis azimuth angle in the sample being measured, this information is not always necessary or of interest. In such cases, it may be omitted without deviating from the spirit of the invention.

Returning to FIG. 1, illuminator 101 directs light along an optical axis 109 towards a sample 106, through a left hand circular polarizer comprising linear polarizer 102 and quarter wave plate 103, and through condenser lens 105. Light is gathered by objective 107 and directed towards beamsplitting apparatus 110, which divides the light into three sub-beams with distinct optical axes 115a–115c, through elliptical polarization analyzers 111a–111 c, to form sub-images 114a–114c at detector 116. In this case, detector 116 is a single CCD detector, but it can equally well be constructed using several CCD detectors, positioned to respectively receive each of the sub-images.

A processor 117 in communication with the detector receives the signal levels from element 116 and performs the calculation of optical retardance based on the signal levels of the various sub-images. Optionally, this processor is also in communication with the elliptical polarization analyzers, to control or alter their function, and may further direct an operator or a mechanism to insert and remove samples from the optical path for background measurements and calibration measurements. Also, processor 117 typically is connected to a display, shown here as 118, which can provide reports on the measurement process, or which can display images of the sample, and the like. In the case where this invention is practiced on a microscope or in a medical setting, this display may optionally be a head-up display or a display that projects the sample information from processor 117 into the microscope field-of-view for the convenience of the operator.

The sub-images may then be analyzed using the algorithms and analysis techniques in the concurrently-filed, co-pending Shribak and Oldenbourg U.S. patent application, or in the Oldenbourg and Mei U.S. Pat. No. US 5,521,705, or comparable algorithms which achieve the same end, namely the use of elliptical analyzer polarizers to deduce the retardance of low-retardance samples. A good discussion of these is also given in "Techniques For Fast and Sensitive Measurements of Two-Dimensional Birefringence Distributions", M. Shribak and R. Oldenbourg, *Applied Optics*, 42 (16), pp. 3009–3017 (2003), which is hereby incorporated in its entirety by reference herein.

In general, the data analysis process is analogous to that used in analyzing measurements obtained in time-series, and the teachings thereof may be applied directly hereto. However, there are some considerations which come into play in an instantaneous retardance measurement system, which are not present in time-sequential measurements. Careful attendance to these will improve the quality of the data that is obtained, so that the inherent sensitivity to low retardance variations in the sample is not degraded.

First, the data analysis described in the Shribak and Oldenbourg *Applied Optics* paper give equations that may be used to derive the retardance $\delta$ and the azimuth angle $\phi$ from the three measurements of intensity corresponding to the analyzers 111a–111c:

$$A \equiv (I_1 - I_3)/(I_1 + I_2) \quad [1a]$$

$$B \equiv (I_2 - I_3)/(I_1 + I_2) \quad [1b]$$

from which $\delta$ and $\phi$ are calculated as:

$$\delta = 2 \arctan(\{\tan(\chi/2) * [2(A^2 + B^2)]^{1/2}\}/\{1 + [1 - 2(A^2 + B^2)]^{1/2}\}) \quad [2a]$$

$$\phi = \arctan(A/B)/2 - 22.50° \quad [2b]$$

In deriving these expressions, several assumptions were made. First, the extinction of the optical apparatus is presumed to be 200:1 or better. In addition to the requirement this places on the optics, the detector or readout circuitry may have an offset (dark-reading) that may need to be compensated or subtracted off. Second, the full-scale signal is presumed to be the same for all three measurements. That is, any change in signal level is imputed to be due to polarization changes only, not to a change in overall brightness in the signal. This condition must hold for every point in the image, which is a fairly good approximation when the only difference between subsequent measurements is that the retardance of one or two elements within the analyzer are changed, especially if it is a liquid-crystal based system in which the only change is a difference in applied voltage.

However, in the present invention, the light producing the first signal $I_1$ is produced by a first sub-beam, while the light producing the second signal $I_2$ and third signal $I_3$ come from the other two sub-beams, respectively. Yet there is no guarantee that these three sub-beams will be equal in overall flux; nor that there is equal intensity directed towards all spatial regions of a given sub-image; nor that the energy directed toward points corresponding to a given spatial region will be the same in each of the sub-beams. This can undermine the use of simple equations [1a] and [1b] to derive $\delta$ and $\phi$, since a difference in intensity ($I_1$–$I_3$) may not signal anything about polarization state when analyzed by elliptical polarizer 3 vs. polarizer 1, if it is due instead to unequal partition of energy in the process of the beam division into sub-beams 1 and 3, or to brightness shading in one sub-image, or different brightness shading patterns in one sub-image relative to another.

There are several techniques that can be applied to this problem. First, the optics may be designed with attention to this point, as will be discussed below, to minimize shading across each sub-image and to balance the energy levels in the various sub-beams. Also, one may insert fixed neutral-density attenuators or electro-optical variable attenuators in individual sub-beams to balance signal levels between the sub-beams, or to achieve a desired ratio of signal levels between sub-beams.

Second, one may estimate the partition of energy into each sub-beam, as well as the pattern of brightness shading within each sub-image, using calibration techniques. One simple approach is simply to image light that is nominally unpolarized, or which is polarized with the opposite circular polarization to what will be employed in the measurement; light having this polarization should be preferentially transmitted, rather than extinguished. In either case, a nominally equal intensity distribution should be obtained at each of the three sample images, and to the extent that a different pattern is obtained, one may scale the actual readings to correct for the observed instrumental shading and unequal partition amongst the sub-beams. This is often a one-time calibration for a given optical setup and is therefore neither burdensome nor in conflict with its subsequent use for real-time data acquisition.

If the elliptical polarizers are constructed using liquid crystal elements as variable retarders, as described later, one may set all the polarizers to analyze the same polarization state to balance their response further. That polarization state is normally the polarization state that is present when no sample is in the beam, i.e. the maximally transmissive state.

Third, the background techniques discussed in the Shribak and Oldenbourg *Applied Optics* paper, and elsewhere, may be used here. These techniques involve measuring the signal when the elliptical polarizers are set to their operating state and no sample is present; then using this to calculate and remove the instrumental polarization signature, so that very small sample retardances can be measured accurately. These may be employed in concert with calibrations of intensity response such as that just discussed, or instead of them if the apparatus is sufficiently balanced in its construction.

Comparable equations, and considerations, apply when working with alternative sets of elliptical polarizers that employ N=2, N=4, and N=5 sub-images. In fact, there is an infinite number of possible arrangements, that might employ any number of sub-beams, and such arrangements are expressly understood to be within the scope of the present invention; but the practical pressure is normally towards those systems that use the fewest sub-beams in order to minimize cost and complexity, and to preserve the highest spatial resolution from the detector(s) employed. Thus embodiments that use N=2, N=3, N=4, and N=5 are preferred in most cases, and especially the embodiments with N=2 and N=4 because they make efficient use of the detector area and can employ various symmetries to advantage.

Another reason to minimize the number N when possible, consistent with the measurement requirements, is that the incident flux is partitioned amongst N sub-beams; thus the intensity of each beam is reduced as N increases. The elliptical analyzer polarizers are set to operating points near the extinction point, so yield relatively low transmittance, on average, when a low-retardance sample is being viewed. Thus to achieve good signal to noise ratio, one requires either a high incident flux level or a relatively low divisor N, in order to produce an adequate signal level in each of the N sub-beams. Since the flux level is often determined by external factors, the result is a preference for systems where N is modest.

Figure 2A:
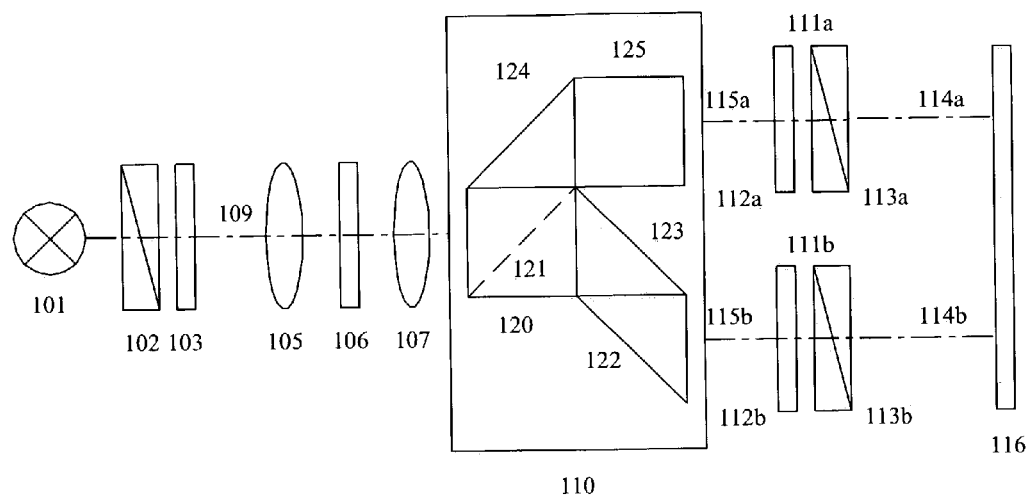
FIG. 2a shows an optical arrangement for practicing the invention using two polarization analyzers, based on partial reflection at a substantially non-polarizing beamsplitter.

Turning now to a specific embodiment from FIG. 2a that uses a DAPR approach, the beam splitter 110 comprises cube beamsplitter 120 with a partially reflecting surface 121; light transmitted by that element passes to right-angle prism 123 and is reflected off its hypotenuse toward right angle prism 122, and reflects off its hypotenuse and proceeds out its other face, to propagate along optical axis 115b. Light that was reflected at partially reflecting surface 121 passes to right-angle prism 124 and reflects at its hypotenuse to cube 125, from which it exits with optical axis 115a.

This arrangement has certain beneficial aspects: first, it provides equal optical path length for the two sub-beams. Second, the sub-beams emerge with optical axes that render them easily directed toward distinct regions of a single detector, or toward distinct detectors, as preferred. In this preferred embodiment, the detector 116 is a Sony ICX-085AL monochrome CCD with 1030×1300 pixel resolution, and a pixel size of 6.8 microns square.

Beam splitter 120 is a critical element in several ways. First, in this embodiment one prefers that it reflect and transmit equal portions of the beam. Second, it is preferable that the reflected portion $R(\phi, \delta)$ and the transmitted portion $T(\phi, \delta)$ not be strong functions of the polarization state. Yet achieving this for reflection from an interface at relatively steep incidence is inherently difficult: one requires that $$R_s = R_p \approx T_s = T_p \qquad [3]$$

and that there be no differential phase delay between the S and P components. One approach is to turn to coatings that are designed with this specific set of requirements in mind. Yet such coatings rarely achieve these conditions fully, and their performance often varies with wavelength. While this type of polarization measurement is often carried out using a source that provides quasi-monochromatic light, such as a halogen lamp with an integral interference filter, it increases the system versatility if the various components are useful over a range of wavelengths.

Another approach is to use an optical arrangement which reduces the incidence angle at the partially-reflecting surface from 45° to something nearer normal incidence. When this is practical, such an arrangement can often yield improved polarization properties.

Note that the specifications are most demanding when the light incident on beamsplitter 120 is circularly polarized, or in any case lies on the 90° longitude line on the Poincare sphere, since in that case the S and P components are equal, and a slight relative difference in reflection (or transmission) between S and P will significantly distort the polarization state of the light thus reflected (or transmitted). Yet this is exactly the circumstance presented when imaging low-retardance samples that have been illuminated with circularly polarized light: when sample retardance is zero, the demands are most extreme.

Figure 2B:
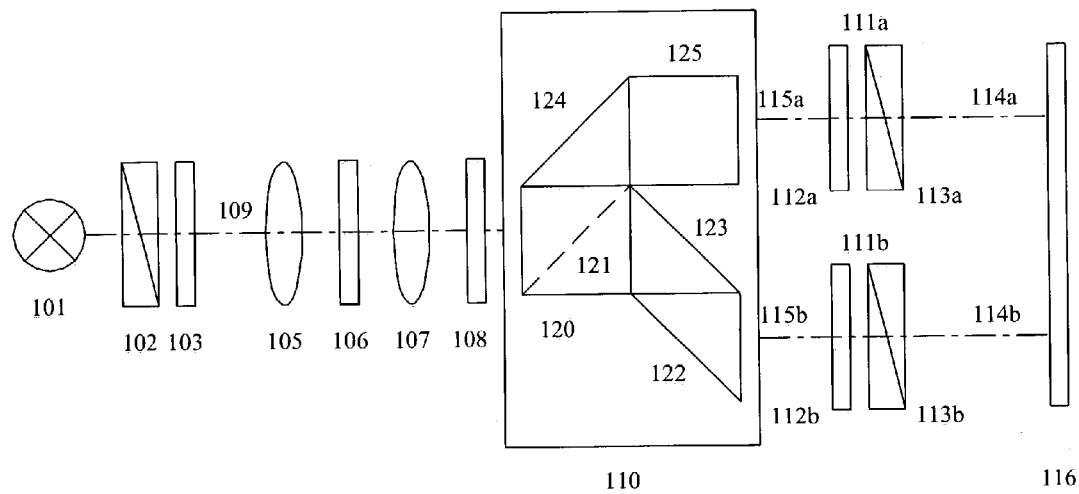
FIG. 2b shows another optical arrangement for practicing the invention using two polarization analyzers, based on partial reflection at a beamsplitter, incorporating a quarter-wave plate before the beamsplitter.

One method of addressing this is illustrated in the preferred embodiment of FIG. 2b. This is like the apparatus of FIG. 2a, except that a quarter-wave element 108 is placed prior to the beamsplitter 120, oriented so that it transforms circularly polarized incident light to be S-polarized at element 120. Since for a low-retardance sample there are only relatively small components of the complementary circular polarization present, there will be relatively small components of the P-polarization. The effect of any disparity between handling of the two eigenstates at element 120 is reduced as well. Indeed, given the trigonometric form of the equations involved, the degree of improvement obtained by addition of quarter wave plate 108 can be greater than the ratio of RH:LH polarization components in the incident beam.

Put most generally, it can be helpful to incorporate one or more waveplates to transform the incident light beam for low retardance samples into one of the eigenstates of the beamsplitter 110. The presence of this element must be taken into account when constructing the subsequent elliptical polarizers 111a–111c, so that they either incorporate an element to undo this transformation, or more commonly, that they use different retarder elements so that the net effect of these elements in concert with 108 is to analyze the incident light into the desired elliptical states. This accommodation, and the accommodation for any geometrical effects that arise from reflection from the beam-steering elements, are understood by those skilled in the art of polarization optics and optical system design.

Another important consideration when selecting beamsplitter 120 is its off-axis performance. Typically, the performance of multilayer coatings varies with angle, especially when the surface is encountered at a steep angle such as the 45° incidence shown in FIGS. 2a and 2b. If $R(\phi, \delta)$ is further a function of incidence angle, the intensity of the various sub-beams can be affected. For example, if element 110 is placed at a pupil plane, then variations in $R(\phi, \delta)$ with incidence angle will be apparent as intensity distributions across the resultant sub-images.

In this preferred embodiment, the other lenses and optical elements are arranged so that the beam is approximately telecentric at element 110. This has benefits not only in terms of the image quality, but it reduces off-axis effects since the chief rays for all points in the image are approximately parallel to the optical axis. Nonetheless, other arrangements may be used.

Figure 3:
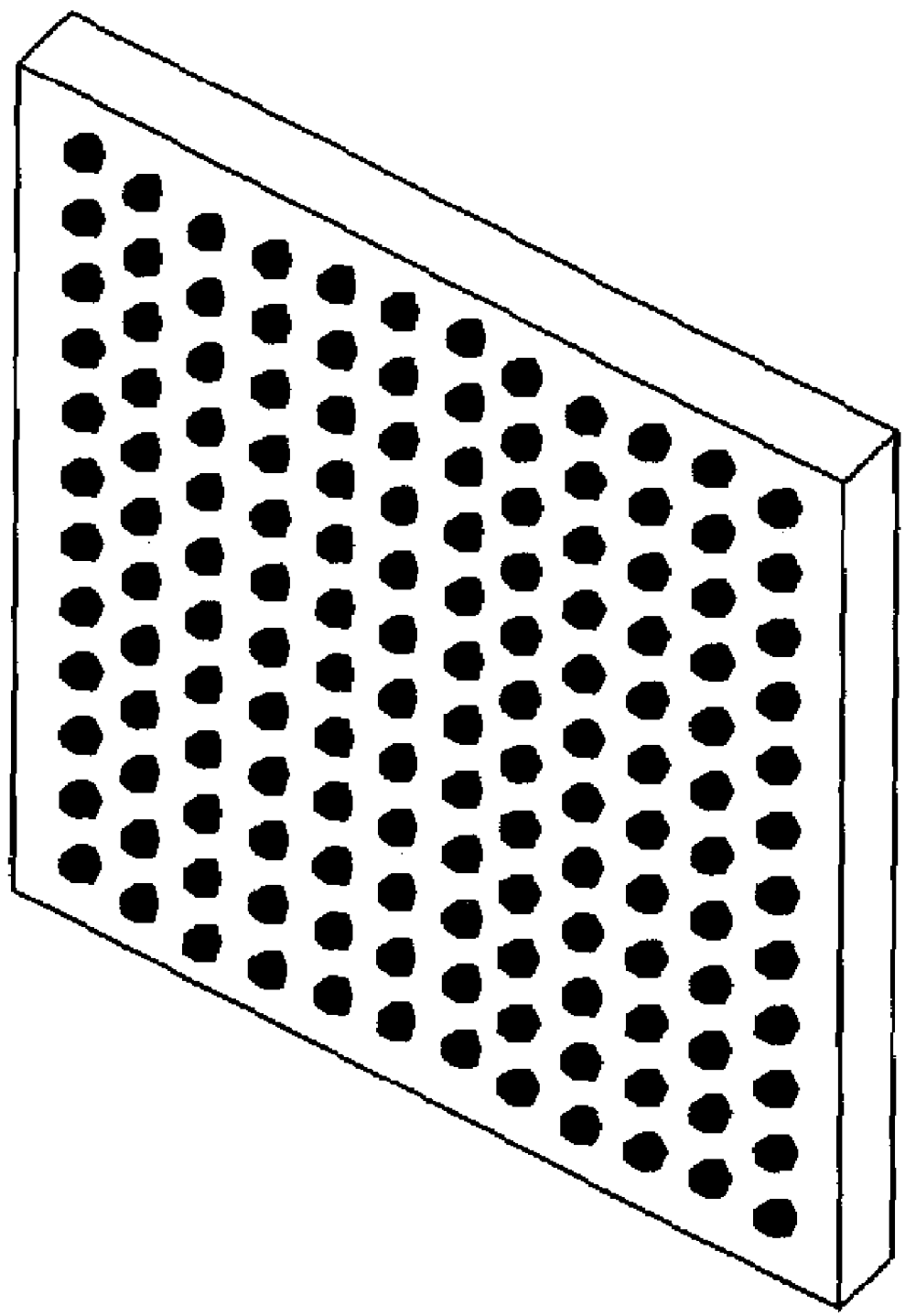
FIG. 3 shows one plate-type beamsplitter suitable for use in the invention.

FIG. 3 illustrates the face of a "polka-dot" beamsplitter. These are sold by Edmund Optics (Barrington, N.J.) but can alternatively be made by vacuum deposition and subsequent photolithographic processing. The part consists of a planar substrate 130, on which have been patterned an array of metal spots 131, typically aluminum. Their spacing and size can be altered but are typically in the range 100 microns. While a regular grid is shown, one could employ a different pattern or an irregular arrangement of spots if the regular grid causes problems due to e.g. diffraction. The choice of spot size and spacing fixes the value of T, and the same factors along with the reflection efficiency of the metal spots, determines R. The splitting action is approximately achromatic, since the geometry is fixed and the reflection efficiency of aluminum varies only slowly with wavelength for much of its useful range. Its angular sensitivity is good, since changing incidence angle does not affect the area fill factor of the spots, and the reflection of aluminum does not vary strongly with angle in the range near 45°. Such an element can be sandwiched between right-angle prisms with optical index matching adhesive, if desired, to create an element that has very little effect on the polarization state of transmitted light.

Another benefit is that the ratio of $R(\phi, \delta)$ to $T(\phi, \delta)$ is well-known and will be stable in manufacturing, as it derives from the lithographic tolerances of the spot pattern, which can be tightly controlled. If this ratio varies from its design value, there will be differences between the brightness of the various sub-beams, which either degrade performance or must be numerically corrected as discussed above.

Thus another preferred embodiment is the apparatus of FIG. 2a using the polka-dot beamsplitter of FIG. 3 as element 120. Another preferred embodiment adds the quarter-wave plate as in FIG. 2b, to transform the incident circularly polarized light to the S polarization when it encounters beamsplitter 130. To minimize shadowing effects, it is desirable to place the polka-dot surface at a substantial distance d from any image planes in the system such that d is large compared with ss/NA, where ss is the polka dot spot size, and NA is the numerical aperture of the system at that point. In this preferred embodiment, the NA is 0.022, the spot size is 0.10 mm, and the beamsplitter is located 40 mm from an image plane. But other arrangements are possible, as long as the pattern of the polka dots does not intrude on the retardance image.

Figure 4A:
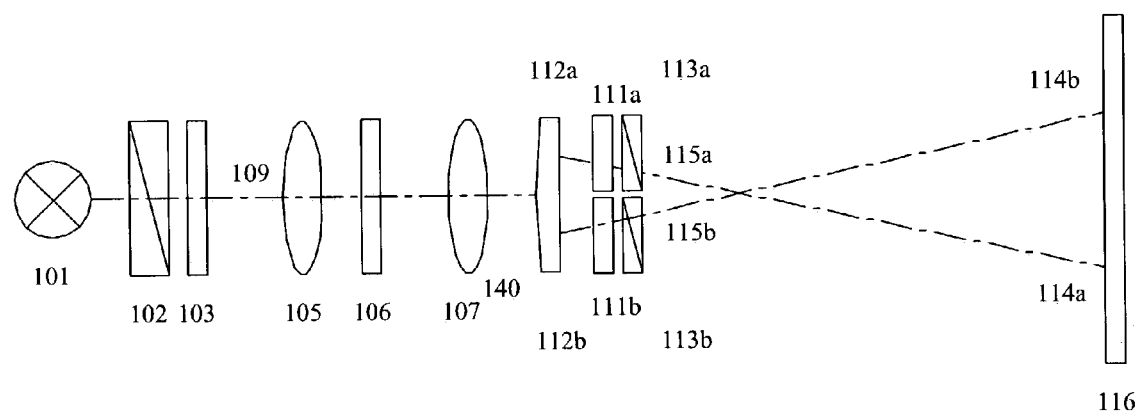
FIG. 4a shows an optical arrangement for practicing the invention, based on refraction at a single multiple-facet prism.

A different approach to beamsplitting is shown in the preferred embodiment of FIG. 4a, which uses a multi-facet optical element 140 to create two sub-beams that propagate along optical axes 115a and 115b towards images 114a and 114b on detector 116. Although relatively steep angles are shown here for the facets of element 140, and thus by Snell's law for the angle between optical axes 115a and 115b, this figure is schematic only, and it is possible to use angles that are steeper or shallower depending on the overall length desired for the apparatus.

In this embodiment, the elliptical retarders 111a and 111b are placed just after the multi-facet optical element, and are arranged so that all the light contributing to image 114a passes exclusively through retarder 111a; and all the light contributing to image 114b passes exclusively through retarder 111b.

It is often desired to place element 140 at or near a pupil plane, in which case the beam is split essentially by division of numerical aperture. In the limiting case, there is no vignetting across the image, i.e. the image produced by the left facet is not systematically brighter at one side or the other, and similarly for the right facet. In practice, there is a mixture of numerical aperture division and some intensity variation across the image, as will be evident by ray-tracing the system using standard design software such as Zemax (Zemax Development Corp, San Diego Calif.) or Code V (Optical Research Associates, Pasadena Calif.).

Often, the pupil is coincident with the objective 107, or that pupil as it is relayed by other optical elements that are present in the system. The pupil locations in a system are readily located using standard ray-tracing software just mentioned, for the particular optical arrangement at hand.

In any case, the elliptical retarders have finite thickness, as does element 140. So there must be some extent along the optical axis spanning the pupil, the facets of element 140, and the faces of the elements that comprise 111a and 111b; accordingly, not all can be strictly coincident, and it is necessary to provide some baffling to prevent cross-contamination of sub-beams. Thus one must expect some unevenness in the illumination levels across the spatial extent of sub-images 114a and 114b. This can be measured and corrected using the calibration method described above;

or if it is small enough, it can be compensated by the background measurement with no sample present, as described in the articles and patents cited.

Figure 4B:
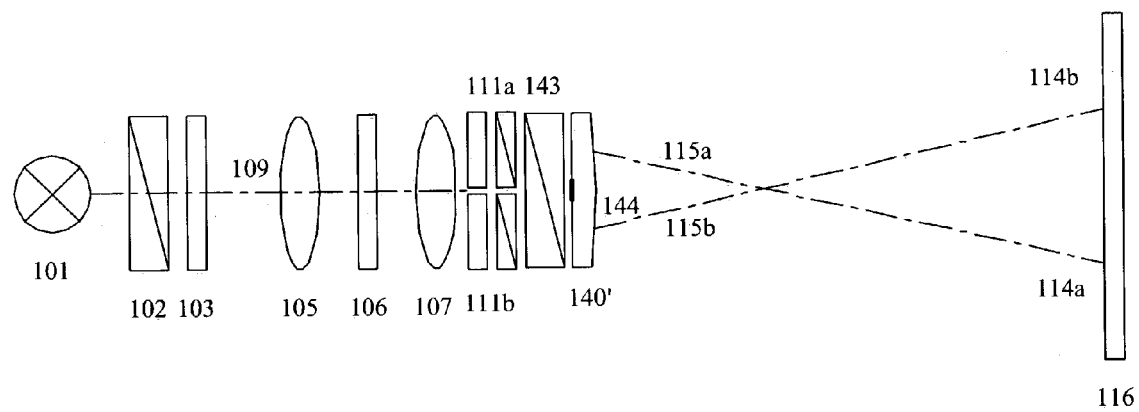
FIG. 4b shows another optical arrangement for practicing the invention, based on refraction at a single multiple-facet prism.

FIG. 4b shows another aspect of the invention. It uses a single multi-facet optical element 140' located after the elliptical polarizers. Such an arrangement has the property that light presented to element 140 is always in the same polarization state, regardless of the polarization of incident light beam or the sample retardance. Any differences between $R(\phi, \delta)$ and $T(\phi, \delta)$ are thus immaterial since the light encountering the element 140 has constant $\phi$ and $\delta$. Similarly, field-of-view effects at this element have only a very weak effect on system performance, dictated by their transmission efficiency rather than their polarization neutrality.

Baffle feature 144 blocks light from passing through one elliptical polarizer and then proceeding through the opposite vertex of 140'. The size required for this baffle depends on the configuration of rays as they pass through these elements, and the proper sizing can be readily determined using a ray tracing program. The baffle may be constructed as an integral part of element 140, in which case it may be convenient to realize it as a patterned metal feature; or it may be a separate mechanical baffle element, according to what is practical given the other aspects of the apparatus.

It can be preferable to choose a specific orientation of the elliptical polarizers 111a and 111b relative to the facets of element 140'. Specifically, multi-facet optical element 140' has eigenstates of polarization, given by the S and P states of its constituent facets, and for the case where one has N=2 or N=4 facets, these can be made coincident with the polarization leaving polarizers 111a and 111b if desired.

This embodiment shows element 140 as planar on one face and multi-faceted on the other. The piano side is shown as facing the detector in FIG. 4a, and facing the opposite way in FIG. 4b. Both arrangements are possible, and indeed one could put facets on both surfaces if desired. The decision to orient element 140 one way or the other may be made based on concerns such as optical aberrations and the like, and may be evaluated using ray-tracing software; or may be made on mechanical mounting considerations, or any factor which proves important in a given application.

It is also possible to incorporate a lens surface in element 140 or 140', so that it acts as a lens and beamsplitter at once. Also, one may create a multi-faceted optical element whose facets are not strictly flat, but incorporate some optical figure to correct aberrations or perform some other desired optical function. Practicality, economy, and the optical considerations of a given design will determine when this is preferred.

The facet size can be used to alter intensity distribution, as a larger facet will direct a larger portion of the beam to a given sub-beam and thus, a given sub-image.

Figure 5:
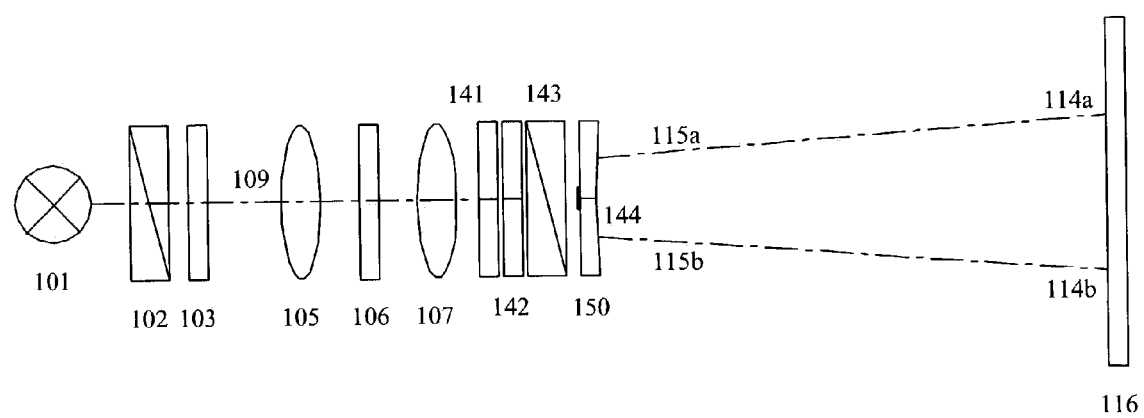
FIG. 5 shows an optical arrangement for practicing the invention based on refraction at several prism slices.

FIG. 5 shows a system that incorporates a hybrid multi-faceted optical element 150, comprised of two wedges joined along the optical axis. This arrangement can provide for a shallower angle between the optical axes 115a and 115b, since the beams need not cross. Image flatness can be more readily obtained, especially in high-NA optical systems or when the instrument must be very compact.

The use of N wedges in a hybrid optical element brings with it a certain complexity: N wedges must be built and then subsequently assembled in tight mechanical registration, and this is an unpleasant aspect of this design. However, the individual wedges can be readily built, whereas conventional lapping and polishing do not provide an easy method for making a single multi-faceted optical element which is thinnest where the facets meet. However, for the case of N=2, and to a limited extent for other values of N, one can construct an integral single multi-facet optical element with the same shape as the hybrid element 150, using single-point CNC grinding techniques. This makes it possible to realize the shape of FIG. 5 with a single multi-faceted optical element, eliminating the problems and cost associated with the hybrid element.

Figure 6:
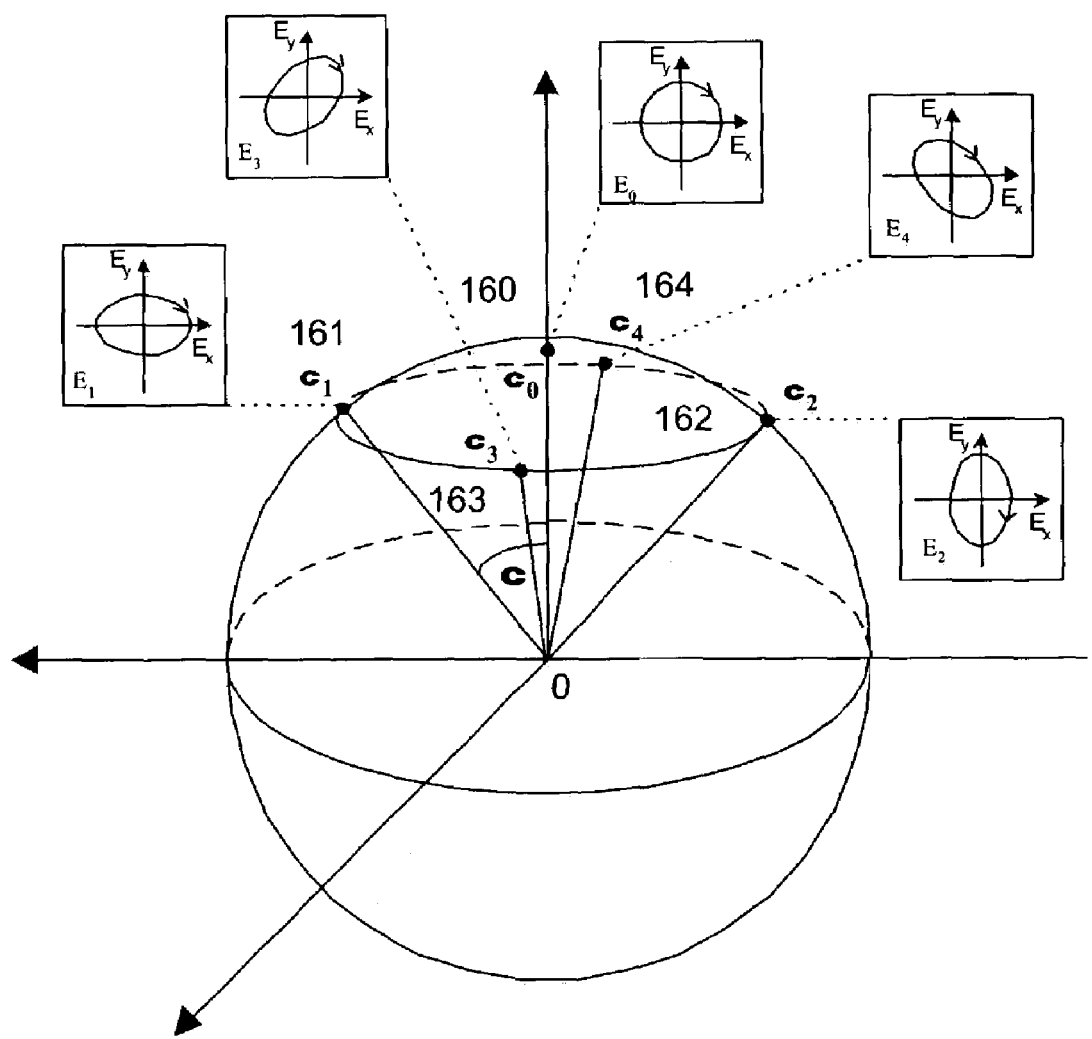
FIG. 6 shows the locations on the Poincare sphere corresponding to the elliptical polarization analyzers for one embodiment of the invention.

FIG. 6 shows the locations of five points on the Poincare sphere, labeled as $\chi_0, \chi_1, \chi_2, \chi_3$, and $\chi_4$, and numbered 160, 161, 162, 163, and 164. The first of these is located substantially at the North pole on the Poincare sphere, while the others are located at a latitude of $90°-\alpha$, equally spaced in longitude. These locations are shown as 0, 180, 90°, and 270°, but could also be offset by an angle x if desired. Practical considerations mean that the actual states may somewhat different from the nominal values diagrammed, but will lie in the vicinity of the points shown, and the invention functions nonetheless.

In the present invention, $\alpha$ is typically 35° or less, and often it is 20° or less. Locating the points closer to the pole has the effect of increasing the sensitivity for small sample retardances, although this limits the dynamic range of the system. Since this dynamic range must be sufficient to cover the instrumental polarization signature which is measured in the background images, as well as the sample retardance, the choice of exactly what polarization states are used will depend on the optical properties of the apparatus as well as the samples to be imaged. The allocation of dynamic range to instrumental effects can be reduced in some cases by calibration, as described above.

The polarization states indicated in FIG. 6 are used when the sample is illuminated with left-hand circular polarized light, i.e. light located at the South pole on the Poincare sphere.

In the preferred embodiments, the N elliptical polarizers are chosen from among the 5 states illustrated in FIG. 6.

One preferred embodiment has N=2 and uses states 161 and 163. Other choices with N=2 are possible, such as using states 161 and 164; however, note that these choices are equivalent to the case of using 161 and 163 with the rotation by a constant angle, such as x=−90° in this example. This illustrates the general case that one may rotate the chosen states by an angle x without difficulty, albeit with the corresponding change that the slow axis azimuth is altered by x/2, and must be corrected accordingly if the azimuth information is used.

Another preferred embodiment has N=3, and uses states 161, 162, and 163. As in the case N=2, there are equivalent choices which differ by a constant angular offset, and these may be used as well.

Embodiments with N=4 are possible in two ways. One possibility is to use states 160, 161, 162, and 163, or the rotated equivalents. This provides a state which is nominally at extinction when the sample retardance is zero.

Another possibility with N=4 is to omit state 160, and use states 161–164 or rotated equivalents thereof. This has the benefit of improved sensitivity and reduced noise, since all four measurements contribute with equal statistical weight to the final measure of retardance. However, for best operation in this case, the optical apparatus should have good extinction, and if this is not the case, the first N=4 embodiment may be preferred. If there is doubt about which alternative is best, a direct measure of signal to noise can be made.

Figure 7:
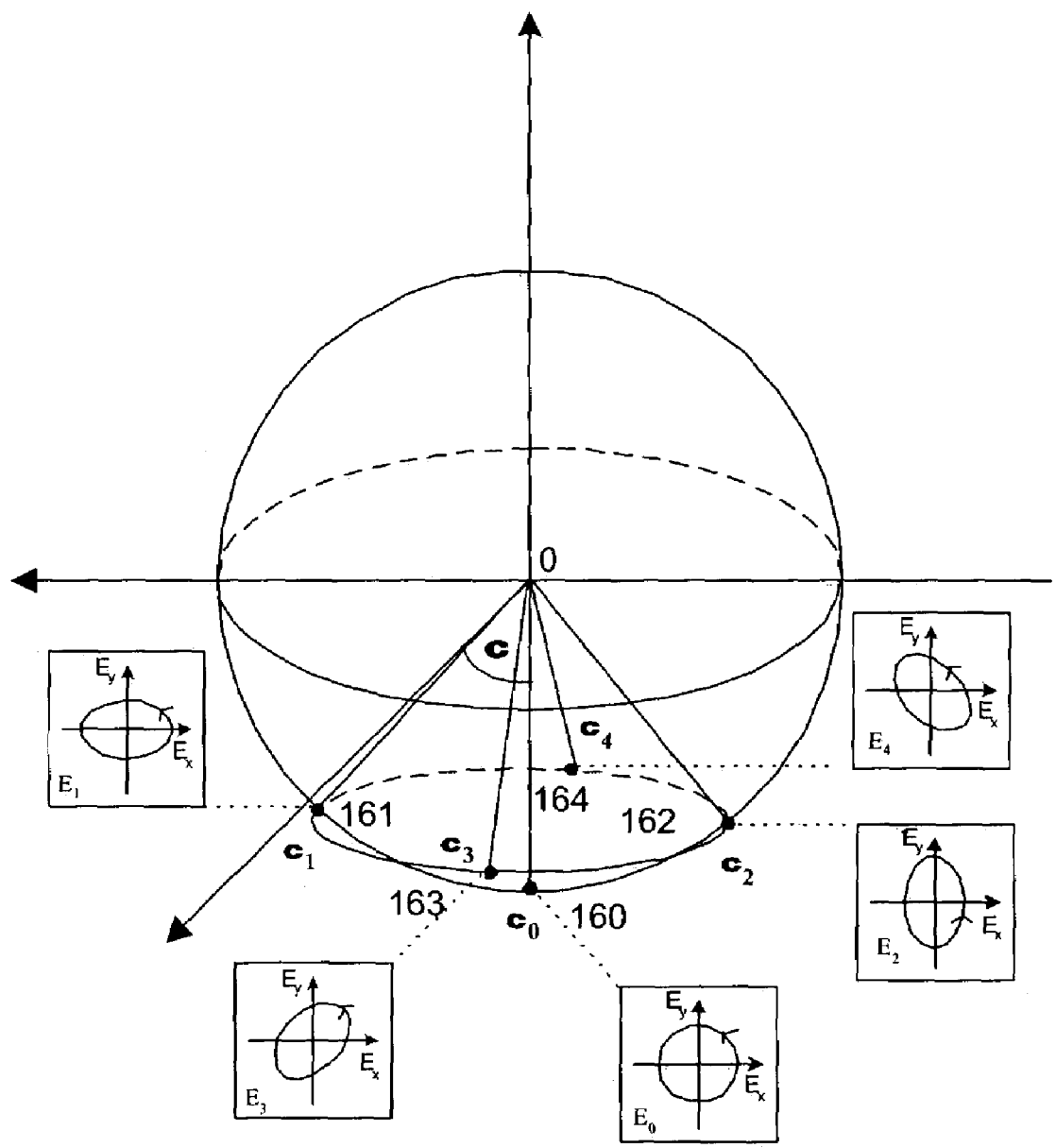
FIG. 7 shows the locations on the Poincare sphere corresponding to the elliptical polarization analyzers for another embodiment of the invention.

FIG. 7 shows a set of locations on the Poincare sphere which are analogous to those in FIG. 6, except that they are situated about the South pole on the Poincare sphere; for measurement of low-retardance samples, the illumination should be right-hand circular polarized. All of the preferred embodiments can be constructed equally well using this set of polarizations if desired.

Figure 8A:
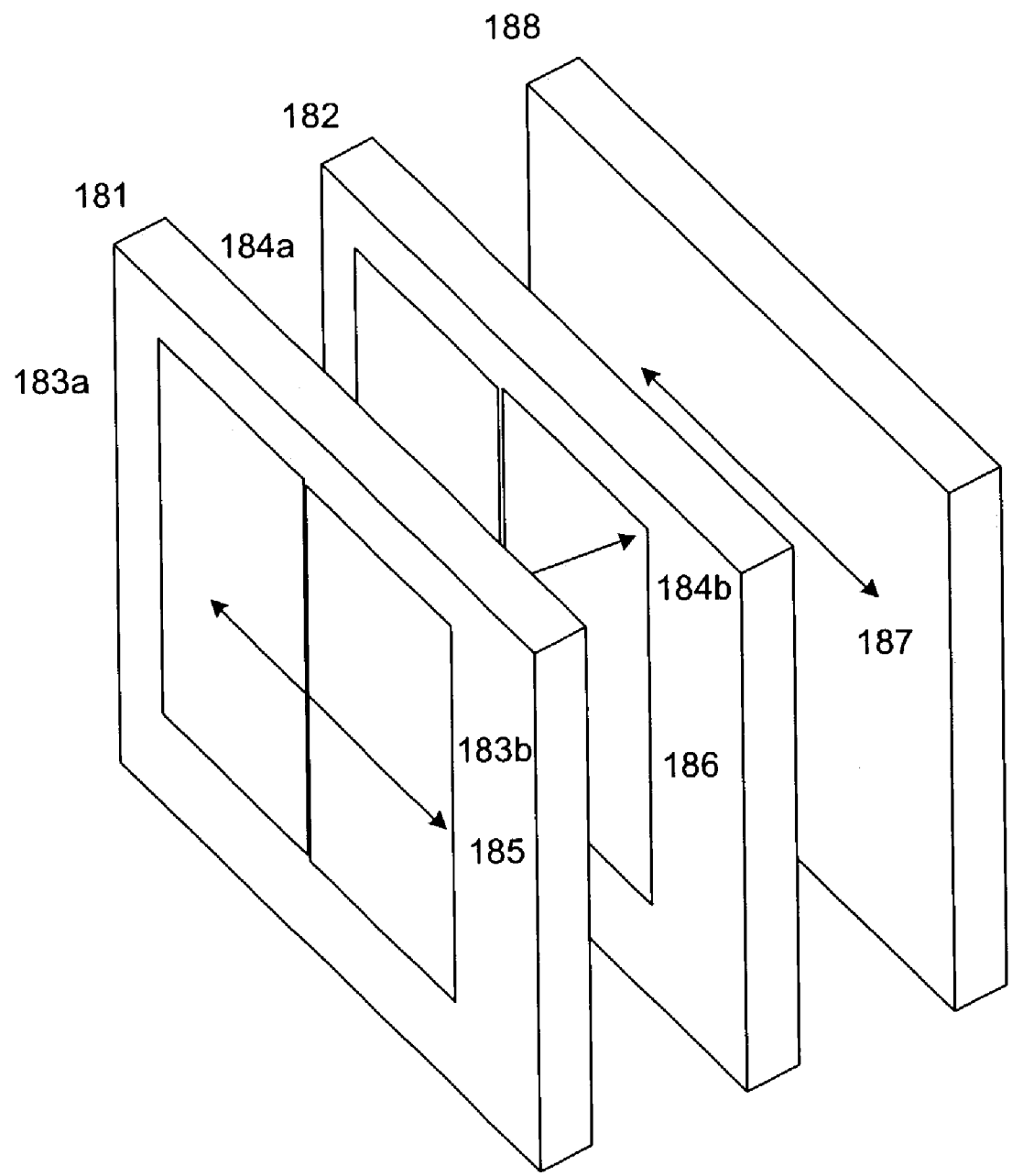
FIG. 8a shows the realization of suitable analyzers using a pair of liquid crystal variable retarders and a polarizer.

FIG. 8a shows one realization of the elliptical polarizers, consisting of liquid crystal variable retarders 181 and 182, each of which has a plurality of pixels that can be driven independently to express different retardances. For liquid crystal retarder 181, these pixels comprise regions 183a and 183b, while for retarder 182 these comprise regions 184a and 184b. The cells are constructed so that the fast axis 185 of cell 181 is oriented at an azimuth angle of 0°, and fast axis 186 of cell 182 is oriented at an azimuth angle of 45°. Linear polarizer 188 has its transmission axis 187 at 0°. This arrangement can produce a target state $S_0$ lying on a pole on the Poincare sphere, as well as four states $S_1$–$S_4$ that are equally spaced in longitude at a common latitude of 90°–α, using the following retardances at the liquid crystal retarders:

TABLE 1

| State | LC retarder 181 | LC retarder 182 |
|---|---|---|
| $S_0$ | λ/2 | λ/4 |
| $S_1$ | λ/2 | λ/4 − γ |
| $S_2$ | λ/2 | λ/4 + γ |
| $S_3$ | λ/2 − γ | λ/4 |
| $S_4$ | λ/2 + γ | λ/4 | where the retardances are specified in terms of waves, and γ=αλ360.

Fixed retarders can be placed in optical series with the liquid crystal retarders, as is known in the art of polarized light optics, to provide equivalent functionality to the states illustrated in this table, or to the mirror image states about the opposite pole of the Poincare sphere.

Figure 8B:
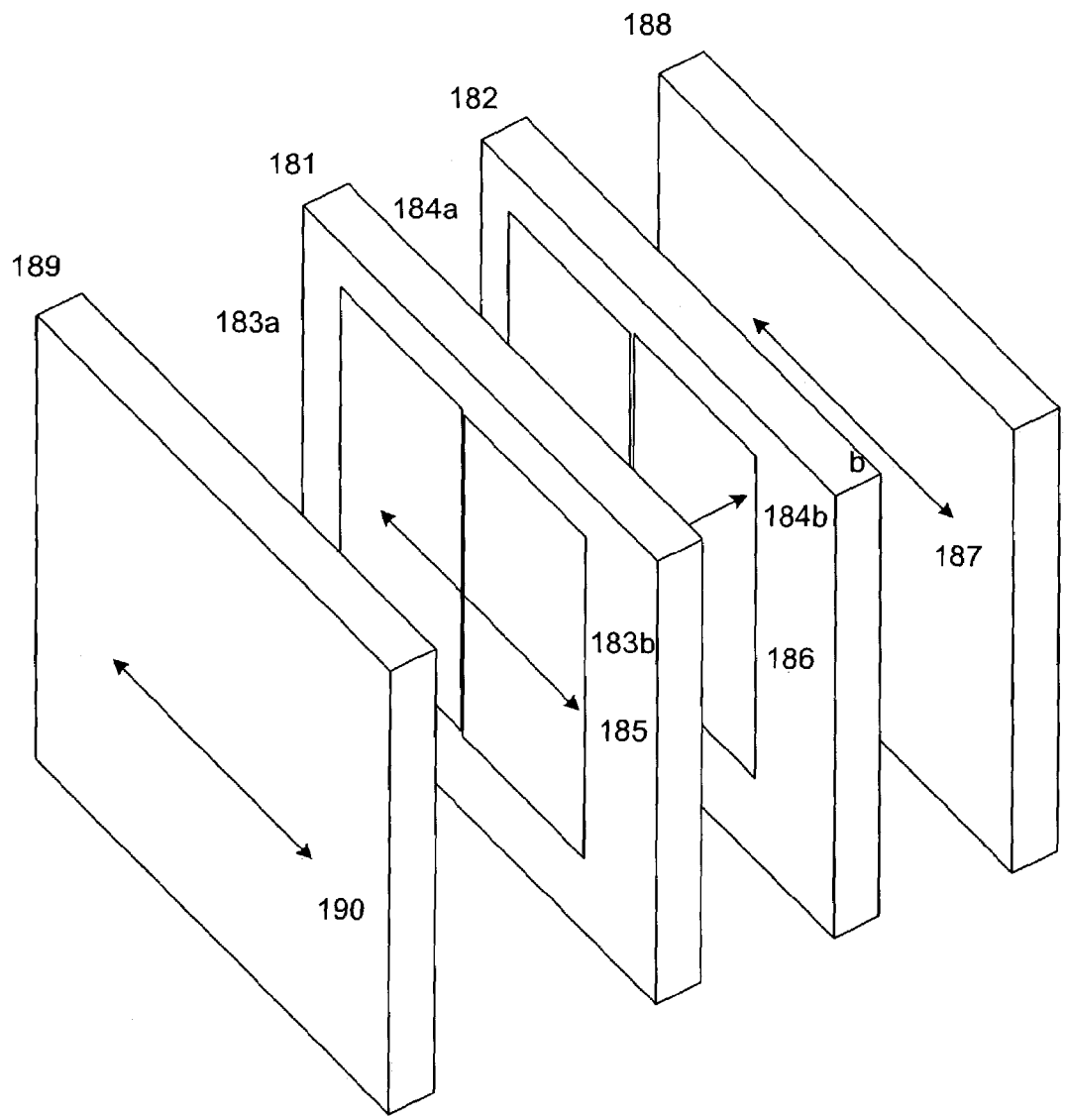
FIG. 8b shows the realization of suitable analyzers using a pair of liquid crystal variable retarders, a fixed retarder, and a polarizer.

For example, in one preferred embodiment shown in FIG. 8b, a fixed retarder 189 with retardance of 0.3 λ is placed adjacent liquid crystal retarder 181, with its fast axis 190 oriented parallel to that of the liquid crystal retarder 181. The retardance provided by LC retarder 181 is then reduced by 0.3λ. This can be beneficial since one may be able to construct a more uniform liquid crystal cell, or one with superior off-axis performance, when its total retardance is reduced.

In another preferred embodiment, a fixed retarder with retardance of 0.2λ is placed adjacent liquid crystal retarder 181, with its fast axis oriented orthogonal to that of element 181. The retardance of the LC retarder 181 opposes that of the fixed retarder, and one may operate with settings of 0.2λ to produce states $S'_0$, $S'_1$, and $S'_3$, and 0.2λ+/−γ to produce states $S'_4$ and $S'_2$, respectively. The primed notation is used to indicate that these states are Poincare sphere mirror images of the states illustrated in Table 1.

One possibility that accrues from the use of liquid crystal retarders is that the elliptical polarizer states can be dynamically changed, typically for calibration purposes. For instance, in one calibration scheme, all of the elliptical polarizers are set to the same state. At this point, the polarization response of the various sub-beams is nominally the same, and the primary difference between sub-images is the residual intensity variation in the beamsplitter and detector apparatus. This enables one to estimate the uniformity of intensity response between sub-images for calibration purposes, as described earlier in this application.

Another technique that the invention provides for is to interchange the assignment of which polarization state is used to analyze a given sub-beam. So, in an N=2 system one might first produce states $S_1$ and $S_2$ in sub-beams A and B, respectively, and obtain the sub-images. Then, in a second phase, one produces state $S_2$ in sub-beam A and state $S_1$ in sub-beam B, and again acquires the sub-images. Next, one performs a calibration that separates the effects of the instrumental partition of energy between sub-beams, and spatially within each sub-image, from the effects of polarimetric differences between channels. Such a calibration is then employed to improve the assessment of polarization state or retardance from the sub-images in future measurements. The interchanging of states and sub-beams is done only at intervals for calibration purposes, and there is no need to do so within each measurement of polarization. The result is an improved real-time measurement of polarization, through better instrumental calibration.

Figure 9:
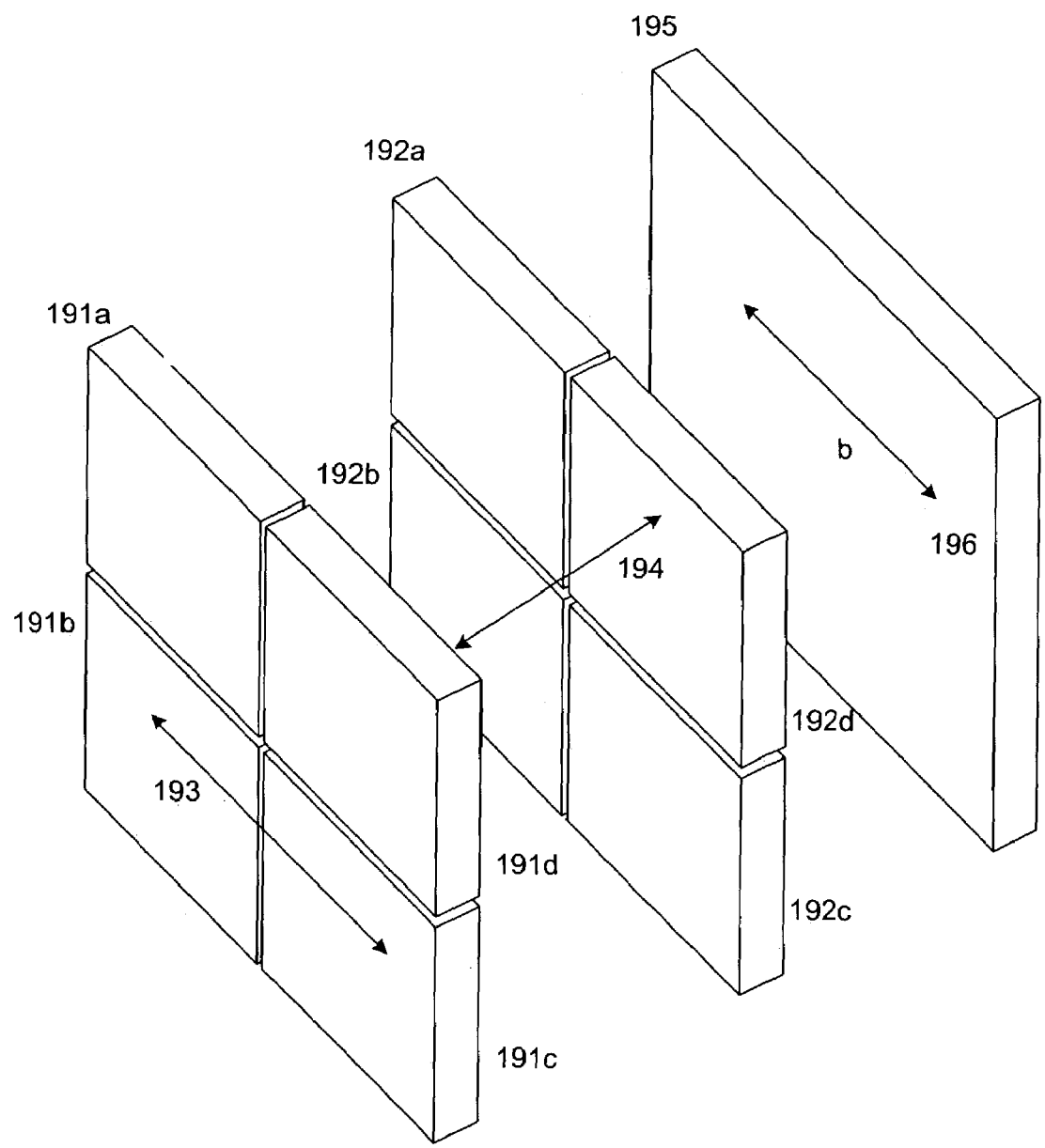
FIG. 9 shows the realization of suitable analyzers using a polarizer and fixed waveplates.

In another preferred embodiment illustrated in FIG. 9, fixed retarders 191a–191d with fast axis orientation 193 of 0°, and fixed retarders 192a–192d with fast axis orientation 194 of 45°, are placed adjacent linear polarizer 195 with transmission axis 196 at 0°. The retardances of these elements are chosen using Table 2, to realize states from among $S_0$–$S_4$. Other states may be chosen that are equally useful, about the other pole of the Poincare sphere, or rotated by an angle x, as described elsewhere in this application.

TABLE 2

| State | LC retarder 191 | LC retarder 192 |
|---|---|---|
| $S_0$ | λ/2 | λ/4 |
| $S_1$ | λ/2 | λ/4 − γ |
| $S_2$ | λ/2 | λ/4 + γ |
| $S_3$ | λ/2 − γ | λ/4 |
| $S_4$ | λ/2 + γ | λ/4 |

Figure 10:
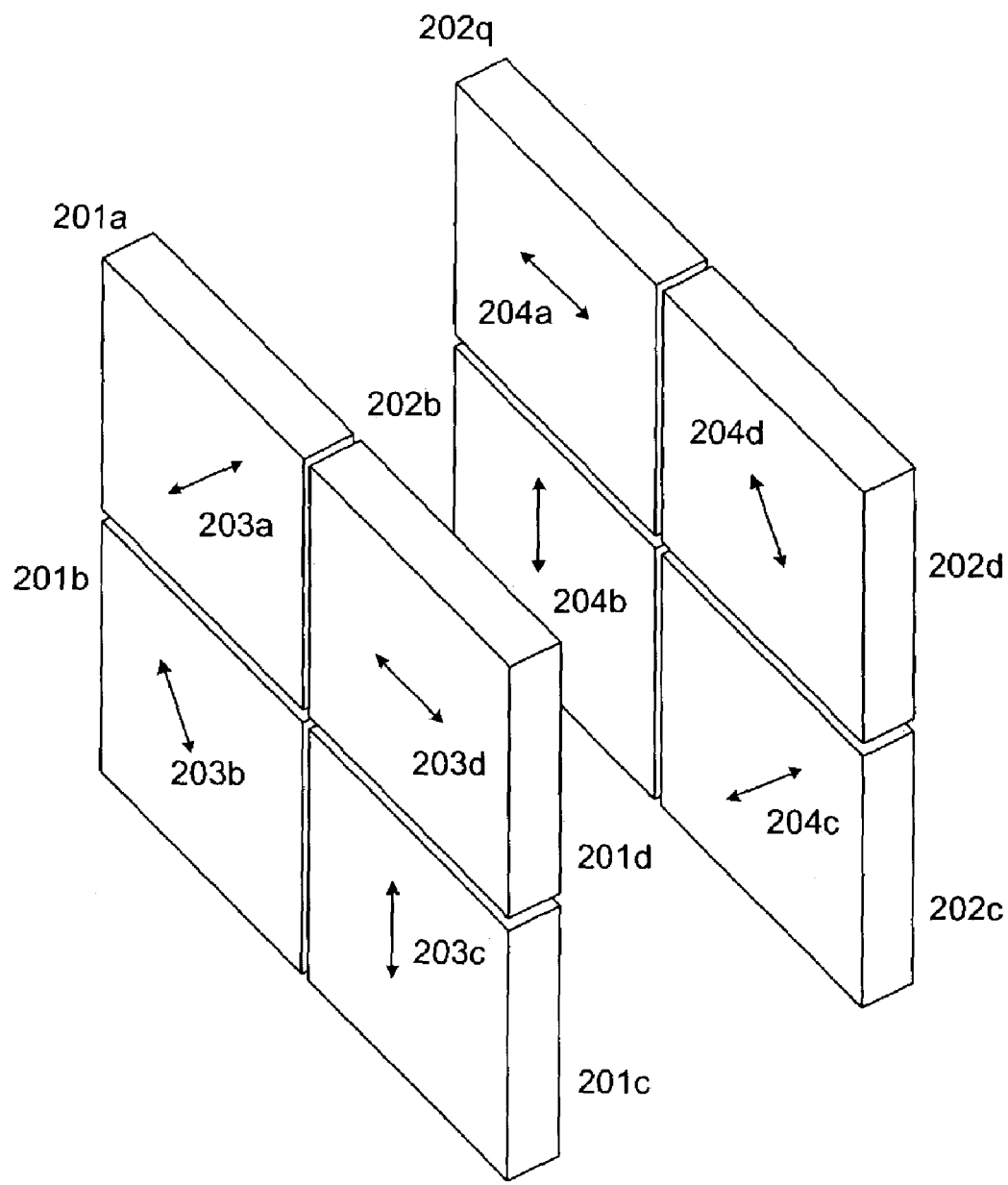
FIG. 10 shows another realization of suitable analyzers using a polarizer and fixed waveplates.
Figure 11:
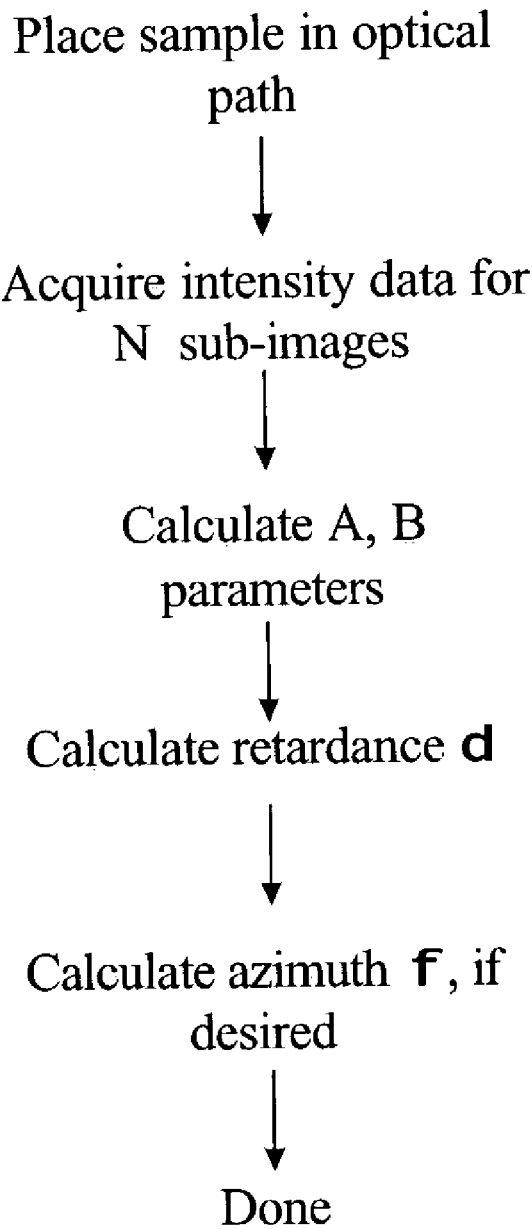
FIG. 11 shows a flow chart indicating an example of an image acquisition sequence.
Figure 12:
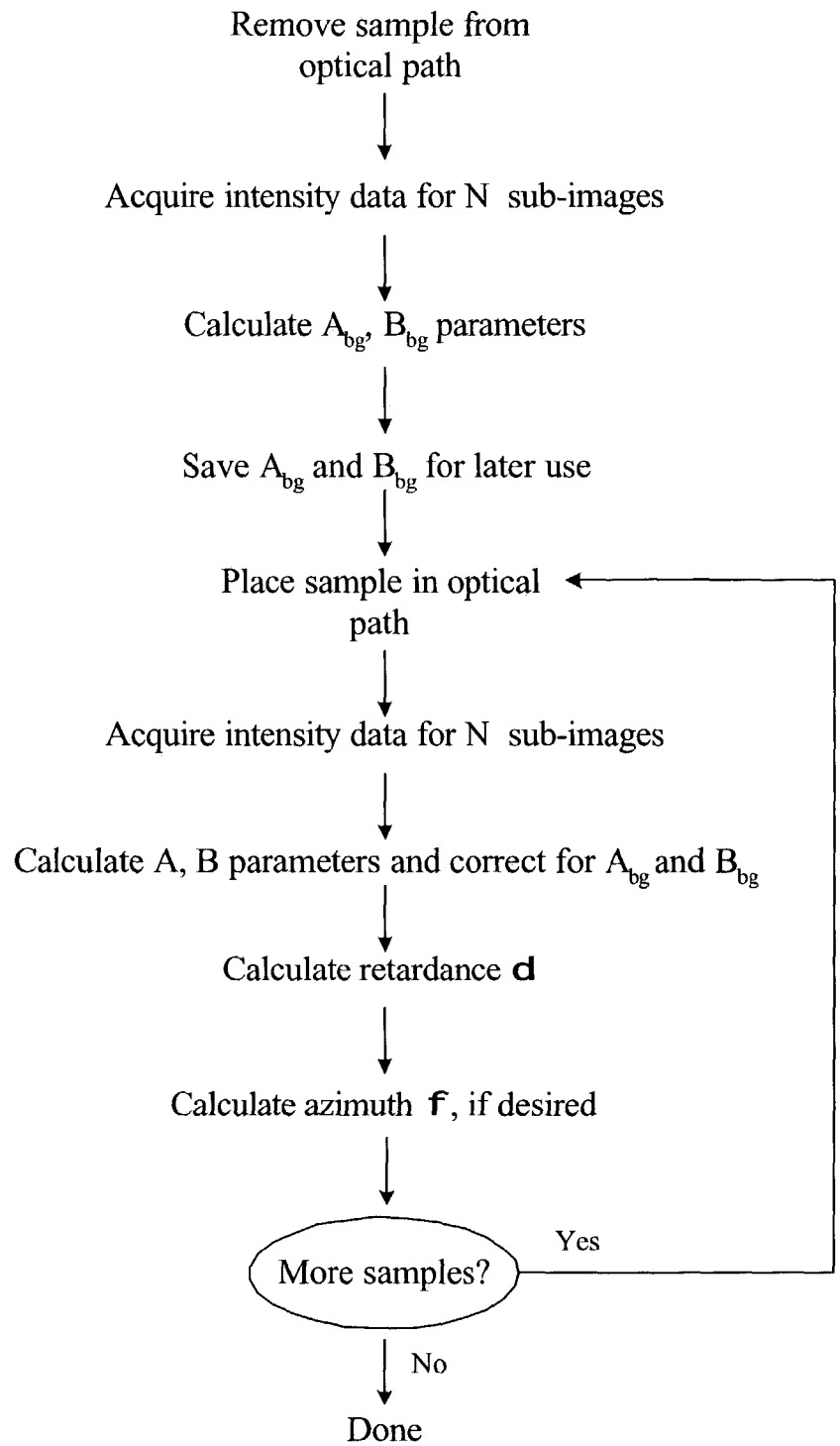
FIG. 12 shows a flow chart indicating an example of an image acquisition sequence with background correction.
Figure 13:
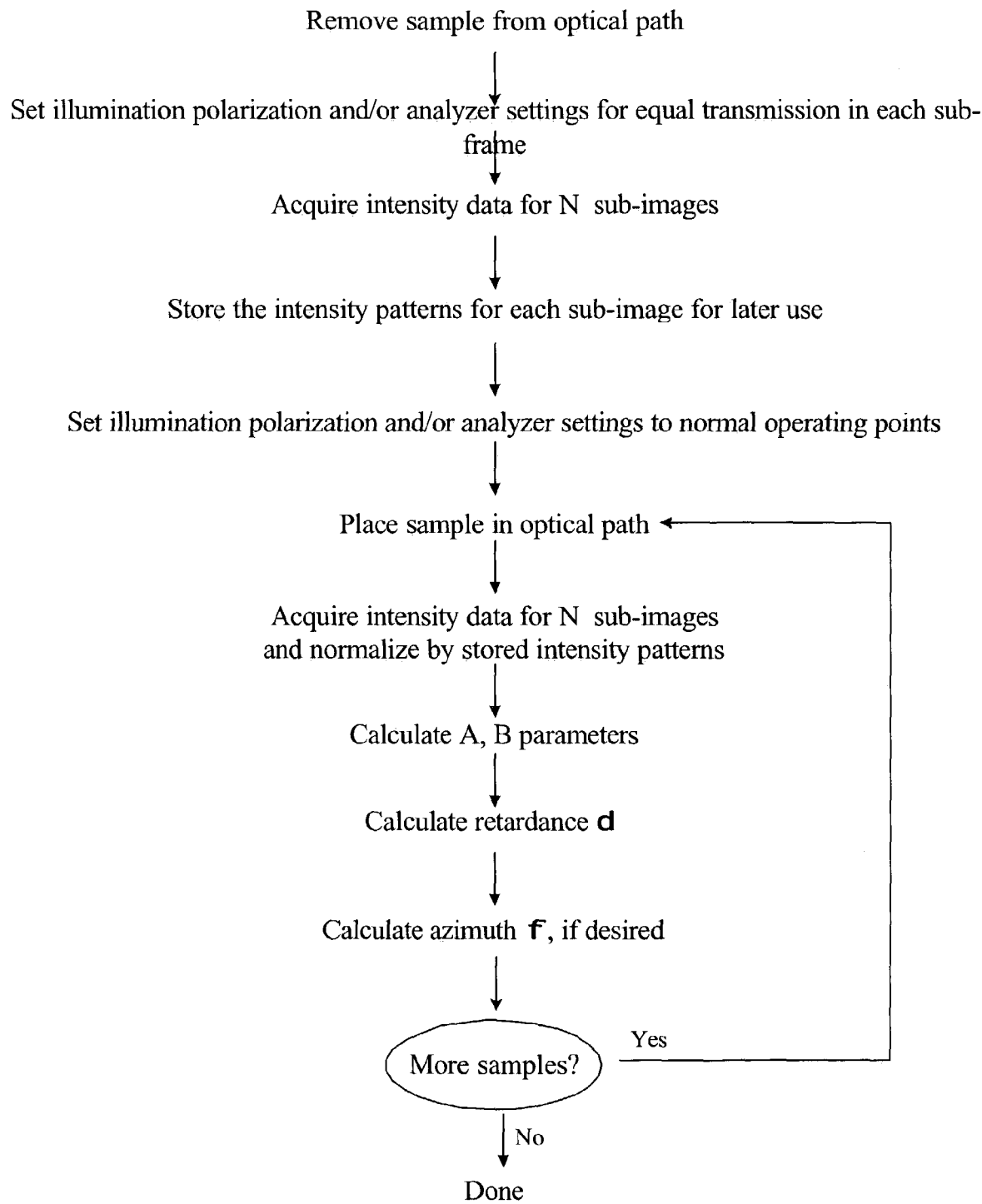
FIG. 13 shows a flow chart indicating an example of an image acquisition sequence using calibration measurement of sub-image intensity.
Figure 14:
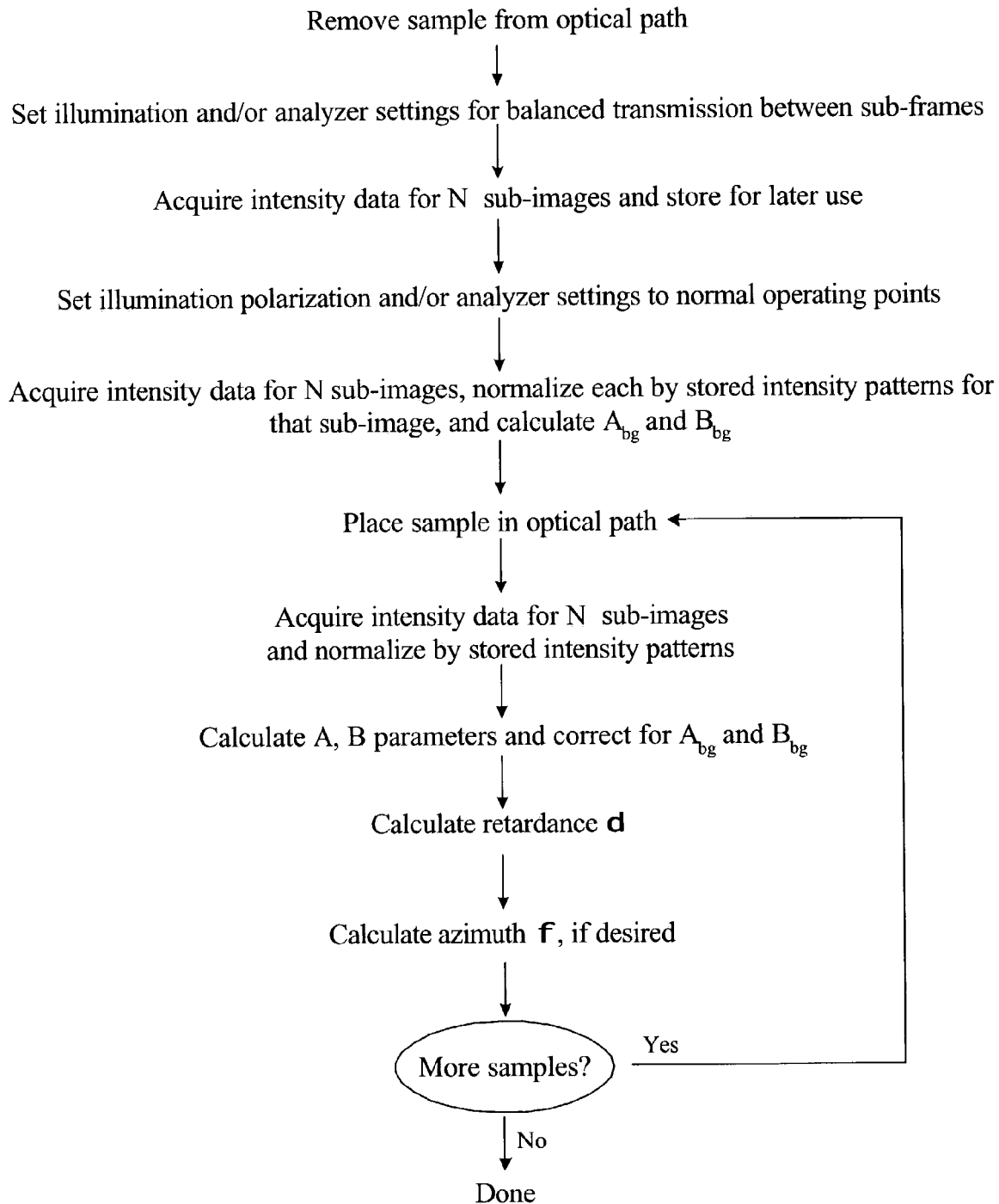
FIG. 14 shows a flow chart indicating an example of an image acquisition sequence using calibration measurement of sub-image intensity, and background correction.

In another preferred embodiment shown in FIG. 10, fixed retarders 201a–201d are placed adjacent to linear polarizers 202a–202d. The retarders have fast axis orientations 203a–203d, and the polarizers have transmission axes given by 204a–204d. For this arrangement, one suitable way to realize state $S'_0$ at a pole on the Poincare sphere, and states $S'_1$–$S'_4$ having constant latitude on the sphere and equally spaced in longitude, is with the following set of orientations and retardance values:

TABLE 3

| State | Retardance of element 201 | Fast axis orientation of element 201 | Transmission axis of element 202 |
|---|---|---|---|
| $S'_0$ | λ/4 | 45° | 0° |
| $S'_1$ | λ/4 − γ | 45° | 0° |
| $S'_2$ | λ/4 − γ | 135° | 90° |
| $S'_3$ | λ/4 − γ | 90° | 45° |
| $S'_4$ | λ/4 − γ | 0° | 135° |

Note that states $S'_1$ through $S'_4$ are all realized using the same elements, though rotated by 90° increments. This can be a practical benefit in assembly, and in obtaining matched values of a within the apparatus.

While these embodiments show several ways to construct suitable elliptical polarizers for use in the present invention, there are alternatives that are equally good, which may be preferred in a given case, based on considerations of materials, available retardances, cost, optical quality, physical thickness, off-axis response, and so on. What is relevant is that one generate a set of states that have the property that one is circular, and the others share a latitude on the Poincare sphere and are equally spaced at 90° intervals of longitude. From these points, one chooses N as described above for construction and use.

While it is possible to construct a real-time polarization imaging system with N>5, such as N=8 with states arranged at 45° increments of longitude on the sphere, considerations of light efficiency and simplicity often argue against this.

Suitable sources of liquid crystal retarders include Meadowlark Optics (Longmont, Colo.) and CRL Opto (Dunfermline, Scotland). Waveplates can be obtained from Meadowlark Optics. Polarizers can be purchased from Nitto Denko (Fremont, Calif.) and the polarizing films division of 3M (Norwood, Mass.).

Instruments constructed in accordance with the present invention are ideally suited for use in the life sciences and medicine, for imaging structures in cells, which typically exhibit sample retardances of 10 nm or less. Typical intracellular structures that have been visualized with the present invention to date include cytoskeletal structures, nuclear structures, and actin filaments. Since no stains or dyes are employed, it is noninvasive and thus especially preferred over alternatives when working with live cells. One case of special interest is the imaging of oocytes as part of in-vitro fertilization, both for research and clinical purposes.

Similarly, tissue sections can be imaged. These have sample retardances that are somewhat higher, though still low—typically 50 nm or less. Examples of tissue that have been shown to be interesting when viewed this way, include skin sections and tissue from burns and wounds, and any tissue where collagen or elastin structure is interesting.

In these applications, a real-time instrument is of markedly higher benefit than a sequential instrument, since living cells move, or undergo changes which can be rapid; and in the case of medical procedures or pathology assessments, the practitioner may not be able to adapt their protocols to the slower pace enforced by an instrument that measures sample retardance sequentially.

In any real-time setting, but especially important in these cases, is the ability to image using a strobed light source, which the present invention affords but which instruments that measure low retardances by sequential measurements do not. This capability enables one to study processes that occur much faster than a single measurement, much as a flash enables a photographer to freeze action that occurs much faster than the camera shutter can open and close.

Accordingly, it is expressly intended that the present invention include the use of the apparatus described above for purposes of imaging live cells and oocytes, as well as tissue.

Similarly, in industrial measurements where low retardance is to be measured, a real-time instrument is greatly preferred.

While specific embodiments have been shown for purposes of illustrating and teaching the invention, it is possible to construct apparatus with other elements without deviating from the spirit of the invention, as will be apparent to those skilled in the arts of optical-design, polarized light, and instrumental design; such variations, combinations, substitutions, alternative embodiments, and equivalents are intended to be within the scope of the present invention. The choice to use one rather than another in any given case may be made using such criteria as cost, complexity, materials availability, size, and the requirements at hand, provided that the aims of the invention are achieved thereby.

Thus, while there have shown and described and pointed out fundamental novel features of the invention as applied to preferred embodiments thereof, it will be understood that various omissions and substitutions and changes in the form and details of the methods described and devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A system for measuring retardance of a sample, comprising
   a sample region for receiving the sample;
   a source of substantially circularly polarized illumination light;
   illumination optics for directing the illumination light toward the sample region;
   analysis optics for receiving incident light from the sample region;
   a plurality of photodetector regions;
   beamsplitting optics for dividing the incident light into a plurality of sub-beams and for directing each sub-beam to a respective one of the plural photodetector regions;
   a plurality of elliptical polarizers disposed in the sub-beams for transmitting incident light whose polarization state lies within a distance $\epsilon$ of a chosen pole on a Poincare sphere; and
   a processor for determining retardance from intensity signals generated at the photodetector regions onto which the sub-beams are directed.

2. The apparatus of claim 1, wherein the sample retardance is 50 nm or less.

3. The apparatus of claim 1, wherein the sample retardance is 10 nm or less.

4. The apparatus of claim 1, wherein $\epsilon$ is 35 degrees or less.

5. The apparatus of claim 1, wherein $\epsilon$ is 20 degrees or less.

6. The apparatus of claim 1, wherein the beamsplitting optics comprise a beamsplitter configured to operate by partial reflection at an interface for dividing the incident light into the sub-beams.

7. The apparatus of claim 6, wherein the beamsplitter is substantially polarization neutral.

8. The apparatus of claim 6, wherein the beamsplitter is a polka-dot type.

9. The apparatus of claim 1, further comprising an optical retarder disposed adjacent an entrance face of the beamsplitting optics for transforming the polarization state of light passing therethrough.

10. The apparatus of claim 1, wherein the beamsplitting optics comprises a plurality of prism facets which divide the incident light into the sub-beams according to the area of each facet.

11. The apparatus of claim 10, wherein the beamsplitting optics comprises a single prism with multiple facets.

12. The apparatus of claim 10, wherein the beamsplitting optics comprises an assembly of a plurality of prisms.

13. The apparatus of claim 10, wherein the elliptical polarizers are located between the sample region and the beamsplitting optics.

14. The apparatus of claim 10, wherein the beamsplitting optics are located between the sample chamber and the elliptical polarizers.

15. The apparatus of claim 1, wherein at least one of the plural elliptical polarizers comprises a linear polarizer and at least one optical retarder.

16. The apparatus of claim 15, wherein the optical retarder is an electrically variable retarder.

17. The apparatus of claim 16, wherein the electrically variable retarder is a liquid crystal cell.

18. The apparatus of claim 1, wherein at least one of the plural elliptical polarizers comprises a fixed linear polarizer and at least two retarder elements.

19. The apparatus of claim 18, wherein at least one of the retarder elements is electrically variable.

20. The apparatus of claim 18, wherein at least two of the retarder elements are electrically variable.

21. The apparatus of claim 1, wherein the plural detector regions comprise a plurality of detectors.

22. The apparatus of claim 1, wherein at least two of the plural detector regions comprise different regions on a single pixilated detector.

23. The apparatus of claim 1, wherein the illumination light source is a pulsed lamp.

24. The apparatus of claim 23, wherein the illumination light source is a flashlamp.

25. The apparatus of claim 1, wherein the illumination light source is operable to emit monochromatic light.

26. The apparatus of claim 25, wherein the illumination light source comprises a broadband light source and a filter.

27. A system for real-time imaging of retardance of a sample, comprising
a sample region for receiving the sample;
a source of substantially circularly polarized illumination light;
illumination optics for directing the illumination light toward the sample region;
analysis optics for receiving incident light from the sample region;
a plurality of photodetector regions;
beamsplitting optics for dividing the incident light into a plurality of sub-beams and for directing each sub-beam to a respective one of the plural photodetector regions;
a plurality of elliptical polarizers located in the sub-beams for transmitting incident light whose polarization state lies within a distance $\epsilon$ of a chosen pole on a Poincare sphere; and
a processor for calculating retardance from intensity signals generated at the photodetector regions onto which the sub-beams are directed;
wherein the sample is one of a biological cell, a tissue sample, and an oocyte.

28. The apparatus of claim 27, wherein the sample is an oocyte.

29. The apparatus of claim 27, wherein the beamsplitting optics comprise a beamsplitter configured to operate by partial reflection at an interface to divide the incident light into the sub-beams.

30. The apparatus of claim 29, further comprising a waveplate located between the sample region and the beamsplitting optics.

31. The apparatus of claim 27, wherein the beamsplitting optics comprise a plurality of prism facets which divide the incident light into the sub-beams according to the area of each facet.

32. The apparatus of claim 31, wherein the plural elliptical polarizers are located between the sample region and the beamsplitting optics.

33. The apparatus of claim 31, wherein the plural prism facets comprise a single prism with multiple facets.

34. The apparatus of claim 31, wherein the plural prism facets comprise an assembly of a multiplicity of prisms.

35. The apparatus of claim 27, further comprising a display unit for providing an image of the sample retardance.

36. The apparatus of claim 35, wherein the display comprises a head-up display.

37. The apparatus of claim 35, wherein the sample is viewable with a microscope and wherein the image of sample retardance provided by the display comprises an image viewed from within the eyepiece of the microscope.

38. A method for imaging retardance of a sample in real-time, comprising the steps of:
illuminating the sample with light that is substantially circularly polarized;
receiving light that has interacted with the sample;
dividing the received light into N sub-beams, where $N \geq 2$;
disposing elliptical polarizers in the N sub-beams, corresponding to states within a distance $\epsilon$ of a pole on a Poincare sphere;
analyzing a polarization state of each of the N sub-beams with the elliptical polarizers;
forming an image of the sample with each sub-beam;
measuring intensity at a plurality of points in the image at each of the N sub-beams; and
calculating the sample retardance based on the N image intensity measurements.

39. The method of claim 38, further comprising the step of calculating a principal slow axis of the sample at a plurality of points.

40. The method of claim 38, further comprising the step of taking a background measurement with no sample present.

41. The method of claim 40, further comprising the step of storing background data derived from the background measurement.

42. The method of claim 41, further comprising the step of correcting the calculation of retardance using the stored background data.

43. The method of claim 38, wherein N is 5.

44. The method of claim 38, wherein N is 4.

45. The method of claim 44, wherein one of the elliptical polarizers transmits received light that is substantially circular in polarization state.

46. The method of claim 44, wherein none of the elliptical polarizers transmit received light that is substantially circular in polarization state.

47. The method of claim 38, wherein N is 3.

48. The method of claim 38, wherein N is 2.

49. The method of claim 38, wherein at least one of the elliptical polarizers is electrically variable.

50. The method of claim 38, further comprising the step of taking calibration images to compensate for variations between optical responses of the N sub-beams.

51. The method of claim 50, further comprising the step of correcting the image intensity measurements using the calibration images.

52. The method of claim 50, wherein one of the polarization of the illumination light and the polarization state of at least one of the polarizers is altered between the calibration measurement and the sample measurement.

* * * * *